United States Patent [19]
Fukuda et al.

[11] Patent Number: 5,824,009
[45] Date of Patent: Oct. 20, 1998

[54] GUIDE INSTRUMENT FOR A MEDICAL NEEDLE WITH THREAD

[75] Inventors: Masatoshi Fukuda; Tadashi Ohtsuka; Haruo Isaki; Kanji Matsutani, all of Tochigi-ken, Japan

[73] Assignee: Kabushiki Kaisha Matsutani Seisakusho, Tochigi-ken, Japan

[21] Appl. No.: 568,346

[22] Filed: Dec. 6, 1995

[51] Int. Cl.⁶ ............................................ A61B 17/04
[52] U.S. Cl. .................. 606/144; 606/139; 606/145; 606/148
[58] Field of Search .................. 606/144, 145, 606/147, 148, 139, 205

[56] References Cited

U.S. PATENT DOCUMENTS

| 14,923 | 7/1856 | Smit | 606/144 |
| 1,037,864 | 9/1912 | Carlson et al. | 606/145 |
| 2,213,830 | 9/1940 | Anastasi | 128/340 |
| 2,365,647 | 12/1944 | Ogburn | 128/340 |
| 3,349,772 | 10/1967 | Rygg | 128/340 |
| 3,470,875 | 10/1969 | Johnson | 128/334 |
| 4,161,951 | 7/1979 | Scanlan, Jr. | 128/340 |
| 4,957,498 | 9/1990 | Caspari et al. | 606/146 |
| 5,254,126 | 10/1993 | Filipi et al. | 606/146 |
| 5,454,823 | 10/1995 | Richardson et al. | 606/148 |

FOREIGN PATENT DOCUMENTS

| 812579 | 10/1936 | France | 606/144 |
| 662602 | 6/1938 | Germany | 606/144 |

Primary Examiner—Michael Buiz
Assistant Examiner—Tina T. D. Pham
Attorney, Agent, or Firm—Townsend & Banta

[57] ABSTRACT

A guide instrument for passing a medical needle with thread through or between body tissues has first and second shafts mounted to be pivotally movable to each other and is formed with, on the first shaft, a needle stand for making the needle with thread stand up and holding the needle with thread, a hole for guiding the thread, and a slit and with, on the second shaft, a needle receiver for receiving the needle when the shafts are made close while the needle with thread stands up at the needle stand. When the shafts 1, 2 are made close while the needle with thread stands up at the needle stand, the needle with thread passes through and between the body tissues and is engaged with the needle receiver. When the shafts are made open, the needle with thread while keeping the engagement with the needle receiver separates from the needle stand, and therefore, the needle with thread can be guided from the first shaft to the second shaft. Where a container for containing the needle with thread is formed in continuation with the needle stand on the parting faces of the first and second shafts, the container can prevent the needle with thread from dropping out, as well as can prevent the body tissues from being damaged by the needle, before the needle reaches an affected area at a time of ligation or suture.

15 Claims, 7 Drawing Sheets

GUIDE INSTRUMENT FOR A MEDICAL NEEDLE WITH THREAD

BACKGROUND OF THE INVENTION

1. Field of the Invention

This invention relates to a guide instrument for a medical needle with thread to perform ligations and sutures by passing a medical needle with thread between or through body tissues of an affected area and by receiving the medical needle that has passed through the tissues and, more particularly, to a guide instrument for a medical needle with thread for performing ligations and sutures by inserting, where a needle attaching a thread to a predetermined position is set to a parting surface at a time that a pair of shafts is in a closed position, the guide instrument to a deep or narrow portion in the patient's body while the shafts are made closed, by then guiding the needle to a ligation or suture portion while the shafts are made open to make the needle up from one shaft, and by transferring the needle from one shaft to the other shaft in association with a closing manipulation of the shafts.

2. Description of Related Art

During a surgical operation, blood vessels surrounding an affected area to be removed may be ligated with thread, or incised areas may be sutured with thread. Such ligations of the blood vessels and sutures of the incised areas can be performed by making a thread pass between or through tissues in hand-manipulating of a needle holder to which a surgical needle with thread is held or of a guide instrument for ligation treatment and by making the thread pulled out of the body to tie a knot.

When conducting ligatures or sutures, a surgeon controls a surgical needle to take it away from the body by switching the manipulating hand of the needle holder from one to the other, after passing the surgical needle through or between the tissues in holding the needle holder in one hand of the surgeon. However, in the case when a portion to be ligated or sutured is located at a deep or narrow area of the body, it is difficult to precisely penetrate such an area and to manipulate the surgical needle to be held by the needle holder again. Therefore, there is a need for developments of a ligation device or suture device to be precisely manipulated by a single hand.

For example, a surgical suture device disclosed in Japanese Patent Publication No. 7-67,457 (WO 93/01750) is developed for the purpose of suturing an affected portion using an endoscope or laparoscopy and is constituted so that, using a needle formed with sharp ends on both sides in a longitudinal direction and a hole for tying a thread for suture at the center of both sharp ends, a pipe clamping the sharp end on one side of the needle is moved toward a clamping mechanism located on the other side by manipulating a grip of the device to clamp the other sharp end by means of the clamping mechanism and so that during this manipulation the thread for suture is made to penetrate the tissues. When using the surgical suture device described above, ligation of blood vessels or suture can be conducted by the grip manipulation of a single step. Such a device is therefore useful to perform a laparoscopic operation in use of a laparoscopy.

With the surgical suture device, however, a suture operation is performed while the surgical needle is penetrated through the inside of the endoscope, and therefore, the device raises problems that drive force must be transmitted in a forward direction for traveling the surgical needle, that the transmission mechanism of the drive force becomes complicated, and that the clamping mechanism and a releasing mechanism for the clamping mechanism become complicated.

In particular, for operations conducted with naked eyes and without any endoscope, such as laparotomy and uterotomy, reliability as of malfunction free and inexpensiveness, as well as good controllability, are important issues, and therefore, there is a need to develop a guide instrument for a medical needle with thread satisfying those demands.

SUMMARY OF THE INVENTION

It is an object of the invention to provide a guide instrument for a medical needle with thread allowing the medical needle with thread to pass through or between body tissues when ligations or sutures are performed in a deep or narrow area in a body.

To solve the problems above, the guide instrument for the medical needle with thread according to the invention makes a medical needle, which comprises a needle body and a thread secured to the proximal end of the needle body extending in an elongated direction of the needle body from the proximal end surface of the needle body, pass through or between body tissues and receives the medical needle that has passed therethrough. The guide instrument is constituted of a pair of shafts pivotally mounted to each other having a handle on the distal end of the shafts for manipulation and is formed with, on the distal end of one shaft of the instrument, a needle stand for rendering the needle body stand up by contacting either or both of the proximal end of the needle body and a part of the circumferential surface located on the proximal side of the needle body and a thread guide for guiding the thread in communication with the needle stand and, on the distal end of the other shaft of the instrument, a needle receiver for receiving the needle body that stands up at the needle stand, whereby while the distal ends of the shafts are made close, the needle body standing up on the one shaft is pushed to pass through or between the body tissues and to be engaged with the needle receiver formed at the other shaft, and while the distal ends of the shafts are made open, the needle body maintains the engagement with the needle receiver to be separated from the needle stand.

The guide instrument for the medical needle with thread (hereinafter simply referred as to "guide instrument") is formed with the needle stand and the thread guide on one shaft (hereinafter referred as to "first shaft"), so that the medical needle with thread (hereinafter referred as to "needle with thread") can be stood up in contact with the first shaft at either or both of the proximal end and a part of the outer circumferential surface located on the proximal side thereof, as well as the thread can be passed through the thread guide. The standing position of the needle with thread brought at the needle stand can be maintained by exerting tension to the thread. That is, the standing position can be maintained by applying tension to the thread under a condition that the needle with thread is in advance rendered to stand up at the needle stand, or by applying tension through the thread to the needle with thread located around the needle stand under a condition that the needle is laid on the shaft to pivotally move the needle with thread with respect to the contact point between the needle with thread and the needle stand and to thereby render the needle with thread stand up.

Since the needle receiver is formed on the other shaft (hereinafter referred as to "second shaft"), the needle with thread can be received by manipulating the first and second shafts in a direction that the distal ends of both shafts come closer to each other and then by engaging the tip of the needle with thread standing up at the needle stand on the first shaft with the needle receiver on the second shaft.

Accordingly, the guide instrument is inserted into a body to render the first and second shafts reach an affected area. Subsequently, where the needle with thread is inserted in the needle stand under the condition that the needle with thread is standing up in advance, the first and second shafts are manipulated so that the jaws of the first and second shafts come to be engaged, or where the needle with thread is inserted in the needle stand under the condition that the needle with thread is laid on the shaft, after the jaws of the first and second shafts are made remote from each other so as to exert tension to the thread to make the needle with thread stand up, the first and second shafts are manipulated so that the jaws of the first and second shafts come to be engaged, and during this manipulation, pushing force is exerted onto the needle with thread standing up at the needle stand to render the needle with thread pass through or between body tissues and engage with the needle receiver, so that the needle with thread is guided from the first shaft to the second shaft, and so that during a disengaging manipulation of the jaws of the first and second shafts, the needle with thread can be released from the first shaft while the needle with thread maintains the engagement with the needle receiver. With the guide instrument thus constituted, the first and second shafts are arranged to pivotally move with respect to each other, and therefore, a surgeon can readily ligate or suture by a single-hand manipulation in the same manner that a surgeon controls forceps.

In the guide instrument, it is preferable that the needle stand formed at the jaw of the first shaft is constituted of a flat surface in contact with the proximal end surface of the needle body or constituted of a recess in contact with either or both of the proximate end surface and a part of the outer circumferential surface located on the proximal side of the needle body. With the guide instrument thus constituted, the first shaft, according to manipulation thereof pushes, in contact with the proximal end surface, the part of the outer circumferential surface, or both of the proximate end surface and the part of the outer circumferential surface of the needle body, the needle with thread which is made to stand up at the needle stand, thereby enabling the needle with thread to pass through or between the body tissues.

It is also preferable for the guide instrument that the needle receiver formed on the jaw of the second shaft is constituted of a long hole having size equal to or slightly less than the diameter of the needle body and that the long hole is formed to extend toward either or both of the proximal and distal sides of the second shaft with respect to a position facing the needle stand formed on the first shaft. With the guide instrument thus constituted, the tip of the needle with thread can be received, in accordance with control of the first and second shafts, while engaged in the long hole. In particular, a formation of a slit extending from the long hole toward either or both of the proximal and distal sides of the shaft, gives a resilient nature to the long hole, thereby enabling the needle with thread to be received surely.

It is further preferable for the guide instrument that a container for containing the needle with thread is arranged on either or both of parting faces of the jaws of the first and second shafts at a position corresponding to the position of the needle stand formed on the first shaft. Arranging such a container for the needle with thread at a position corresponding to the position of the needle stand allows the needle with thread to be contained in the container when the guide instrument is inserted into the body. Therefore, the needle with thread can be contained in the container formed at the parting face between the first and second shafts immediately before a ligation or suture. Accordingly, the needle with thread is not exposed until reaching the affected area, and even when plural guide instruments are prepared for an operation, those guide instruments do occupy only a small area. Since made to reach the affected area while the needle with thread is contained in the container by closing the jaws of the shafts, the needle with thread is never dropped off from the guide instrument during such transportation, and the needle never provides damages to normal tissues. Moreover, the needle with thread can easily reach the affected area even if the affected area is a deep or narrow area in the body.

It is yet preferable for the guide instrument to be formed with a guide for guiding along the first shaft the thread secured to the needle body which is contained in the container or which stands up at the needle stand. Forming such a guide allows thread extending from the needle body stood up at the needle stand or contained in the container to be guided along the first shaft up to the handle. The thread, consequently never becomes entangled with the first shaft when the ligation or suture is conducted. The thread is also smoothly paid out when the needle with thread that has passed through the tissues and been received by the needle receiver arranged on the second shaft is pulled out of the body.

Forming a holding member mounted on the first shaft for holding the thread guided along the first shaft allows the thread, to which no tension for the needle with thread contained in the container is exerted or to which tension for the needle with thread standing at the needle stand is exerted, to be held. The conditions of containing the needle with thread at the container and of standing at the needle stand can be maintained by holding the thread with the holding member in the manner above.

When provided on the first shaft for applying tension to the thread guided along the first shaft, a tension applying member is controlled, at a time that the needle with thread is stood up at the needle stand on the first shaft after the needle with thread contained in the container is made to reach the affected area, to exert tension to the thread, thereby rotating the needle with thread around the corner of the proximal end surface, as a center, which is in contact with the needle stand, to enable the needle with thread to stand up.

It is also preferable to provide on the first shaft a projection for winding the thread guided along the first shaft. Forming the projection allows the manipulation at a time to exert tension to the thread to be easy.

BRIEF DESCRIPTION OF THE DRAWINGS

The above and other objects and features of the invention are apparent to those skilled in the art from the following preferred embodiments thereof when considered in conjunction with the accompanied drawings, in which.

DETAILED DESCRIPTION OF THE PREFERRED EMBODIMENTS

Figure 1:
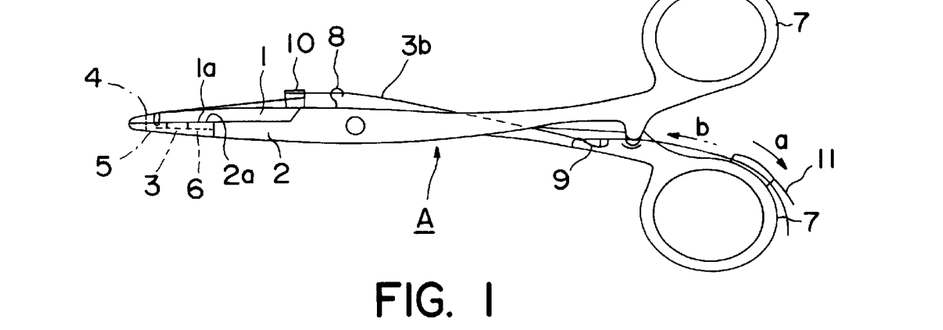
FIG. 1 is a side view showing the entire shape of a guide instrument having a pair of shafts pivotally attached to each other according to the invention.

Referring to the drawings in detail, in particular, to FIG. 1, a guide instrument A according to a preferred embodiment of the invention, is shown. The guide instrument A has a pair of shafts 1, 2 pivotally movable against each other. A needle stand 4 for making a needle with thread 3 stand up is formed on one shaft, or the first shaft 1; a needle receiver 5 for receiving the needle with thread 3 is formed on the other shaft, or the second shaft 2. A container 6 for containing the needle with thread 3 is formed at parting faces 1a, 2a which contact each other when the shafts 1, 2 are made closed. The guide instrument A is entirely in a shape of forceps and is constituted to perform ligations and sutures of affected areas by controlling the guide instrument A in the same manner as forceps.

The needle with thread 3 is constituted of a needle body 3a formed in a straight needle shape having length selectively determined in the range of 3 to 15 millimeters in accordance with the length of the shafts 1, 2 so as not to interfere with opening and closing motions of the shafts 1, 2 and of a thread 3b attached to one end of the needle body 3a. The length of the needle body 3a is approximately set to length equal to or less than one third of the distance between the pivot center of the shafts 1, 2 and the needle stand 4. The needle body 3a constituting the needle with thread 3 includes a tip 3a1 in a pointed shape so as to be capable of easily puncturing the tissues when passed therethrough or in a spherical shape capable of easily passing between tissues, a barrel 3a2 having length capable of adequately engaging with the needle receiver 5 formed on the second shaft 2, and a proximal end face 3a3.

The diameter of the barrel 3a2 is not determined simply but determined, according to the diameter of the thread 3b chosen in accordance with ligations or sutures, to be twice or more of the diameter of the thread 3b. For example, a thread used for ligation or suture is typically of 0.2 to 0.249 millimeters (USPS: United States Pharmacopeia Standards No. 3-0), 0.2 to 0.399 millimeters (USPS No. 2-0), 0.35 to 0.399 millimeters (USPS No. 1-0), and 0.4 to 0.499 millimeters (USPS No. 1). As a result, the barrel 3a2 or the needle body 3a is set to have its outer diameter of 0.7 to 0.9 millimeters in accordance with the diameter of the thread 3b. Thus, the diameter of the needle body 3a is designed to be twice or more of the diameter of the thread 3b, so that the needle body 3a can receive propelling power in contact with the needle stand 4 at the proximal end surface 3a3 or at the outer circumferential surface on the proximal side of the needle body 3a.

The needle body 3a is generally made of stainless steel. The needle body 3a can also be made by injection molding of synthetic resin; in such a case, the needle with thread 3 can be manufactured by a single process by an insertion molding which inserts the thread 3b in the mold. The needle body 3a can further be made of tungsten carbide or titanium alloy. Specifically, if the needle body 3a is made of a magnet, the needle with thread 3 can be easily transferred by providing the needle receiver 5 made of magnetic material. The material forming the needle body 3a is at any event not limited, and can be formed of any material having rigidity penetrable between or through the body tissues and not affecting the human body.

Regarding the needle with thread 3, the needle body 3a and the thread 3b are not necessarily separated and can be a united needle formed with a so-called stainless thread. Such a united needle has the needle body 3a and the thread made of stainless steel; the needle body 3a is hardened to have predetermined hardness by a hardening fabrication or the like; the thread 3b is softened by a thermal treatment.

The needle body 3a is in a straight needle shape as shown in FIG. 7 (a) to (d). The tip 3a1 is formed in spherical shapes as shown in FIG. 7 (a) to (c) in accordance with tissues to be penetrated or in a sharp pointed shape as shown in FIG. 7 (d). When the thread 3b is attached to the needle body 3a, a part of the needle body 3a on a side of the proximal end surface 3a3 may be caulked to reduce its diameter, as shown in FIG. 7 (a), (d), or as shown in FIG. 7 (b) the thread 3b may be made to adhere by means of adhesive or the like without caulking the needle body 3a. Moreover, as shown in FIG. 7 (c), the thread 3b may be attached by being caulked into a tapered shape a portion of the needle body 3a on the side of the proximal end surface 3a3 in certain length.

The needle with thread 3 thus constituted stands up at the needle stand 4 formed on the first shaft 1 and contacts either or both of the proximal end surface 3a3 of the needle body 3a and a part of the outer circumferential surface of the needle body 3a on the side of the proximal end surfaces of the shaft, so that the pushing force accompanied with the manipulation of the first shaft 1 exerts to the contacting area.

Figure 2:
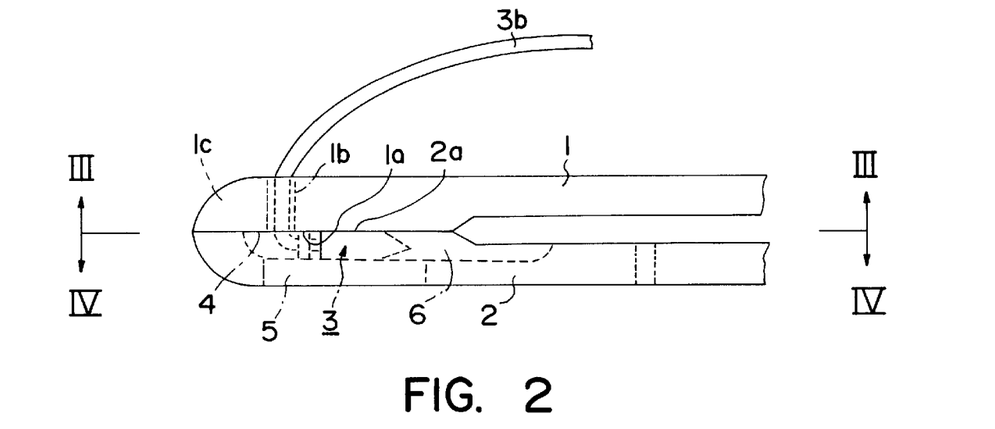
FIG. 2 is a side view showing an essential portion of the guide instrument where a needle with thread is contained at the parting surface of the jaws of the shafts of the guide instrument.
Figure 3:
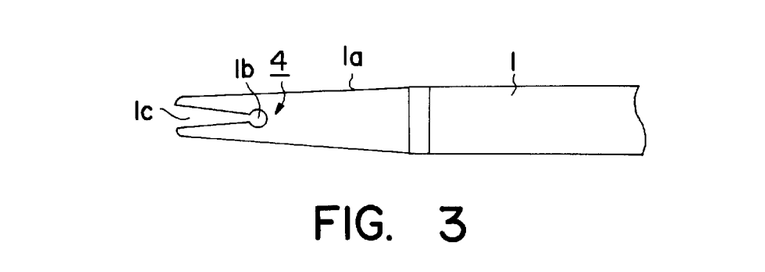
FIG. 3 is a bottom view showing the essential portion of the first shaft of the guide instrument, taken along a line in FIG. 2 when seen in a direction indicated by arrows of III, III.
Figure 4:
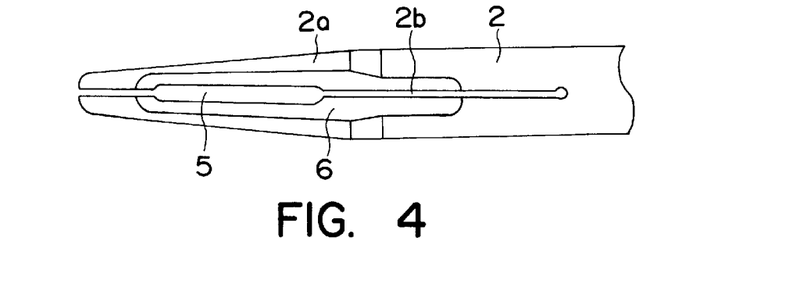
FIG. 4 is a top view showing the essential portion of the second shaft of the guide instrument, taken along the line in FIG. 2 when seen in a direction indicated by arrows of IV, IV.
Figure 5A:
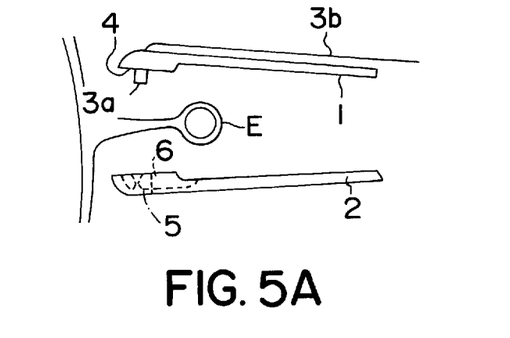
FIG. 5 shows illustrations for describing a manipulation for ligation.
Figure 5B:
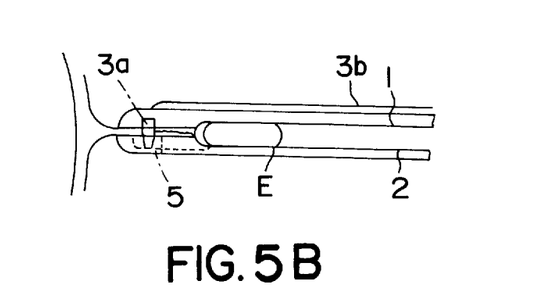
Figure 5C:
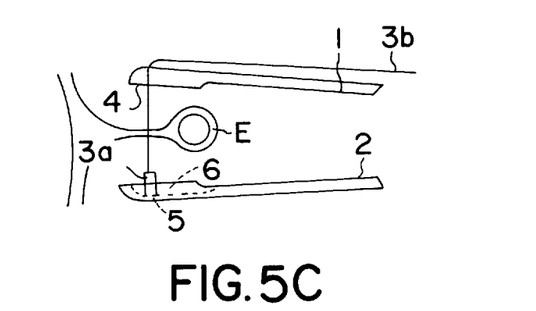
Figure 5D:
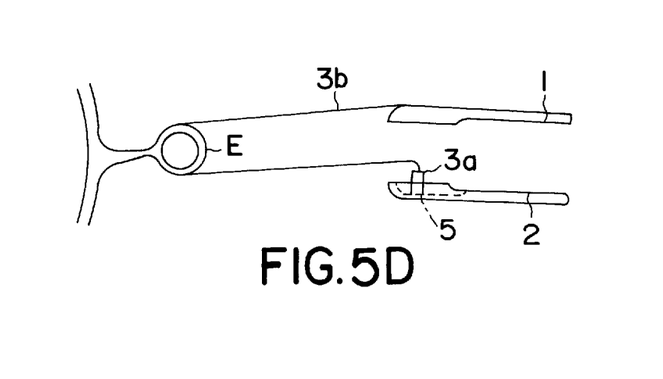

Referring to FIGS. 2 to 4, the essential constitution of the guide instrument A is described as follows. The needle stand 4 is formed at a position certain distance away from the tip of the guide instrument on the parting face of the first shaft 1. The needle stand 4 is formed on a flat surface or a surface having a serrate projections, which has a function to contact with the proximal end surface 3a3 of the needle body 3a to render the needle body 3a stand up.

A hole 1b penetrating the shaft 1 in a thickness direction of the shaft 1 is formed at a position corresponding to the needle stand 4. A slit 1c is formed so as to communicate between the hole 1b and the tip of the shaft 1. The hole 1b has a function to position the thread 3b attached to the needle body 3a of the needle 3 away when the needle with thread 3 is stood up at the needle stand 4. The hole 1b has the diameter less than the diameter of the needle body 3a and greater than the diameter of the thread 3b. The slit 1c functions to guide the thread 3b to the hole 1b and has size capable of easily passing the thread 3b when the thread 3b is set to the guide instrument A. A corner between the hole 1b and the upper side of the slit 1c as opposed to the side of the needle stand 4 is rounded smoothly without any keen edge to prevent the thread 3b from being damaged in contact therewith when tension is exerted to the thread 3b.

With the needle stand 4 thus formed, the proximal end surface 3a3 of the needle body 3a is pushed on the flat surface or serrate surface forming the needle stand 4 by giving tension to the thread 3b passed through the hole 1b, thereby enabling the needle with thread 3 to keep in a standing position thereof It is preferable for the needle with thread 3 that stands up at the needle stand 4 to permit more or less inclinations and positional deviations.

The needle receiver 5 is formed on the second shaft 2. The needle receiver 5 has a function to grasp and receive the needle body 3a when the needle body 3a of the needle with thread 3 that stands up at the needle stand 4 is engaged with the needle receiver 5 at a time of ligation or suture. The needle receiver 5 is constituted of a parting face 2a of the second shaft 2 and is formed in opposition to the needle stand 4 formed on the first shaft 1. That is, the needle receiver 5 is formed, as originated from a position on the second shaft 2 opposed to the hole 1b formed on the first shaft 1, in a long hole shape having width substantially equal to or a little less than the diameter of the needle body 3a of the needle with thread 3 and certain length and penetrating the second shaft 2 in a thickness direction of the second shaft 2, and for the purpose of providing resilient nature to the needle receiver 5, a slit 2b is formed so as to extend in a longitudinal direction across the needle receiver 5 from the tip of the second shaft 2. An edge facing the first shaft 1 in the long hole constituting the needle receiver 5 is preferably formed with a rounded surface so as to permit more or less inclinations and positional deviations of the needle with thread 3 stood up at the needle stand 4.

When the first and second shafts 1, 2 are made close after the needle with thread 3 is stood up while the first and second shafts 1, 2 are manipulated to separate from each other, the tip 3a and the barrel 3a2 of the needle body 3a are pushed into the needle receiver 5. Therefore, the needle receiver 5 can grasp and receive the needle body 3a of the needle with thread 3. Holding force of the needle receiver 5 against the needle body 3a when the needle body 3a of the needle with thread 3 is pushed into the needle receiver 5, is set to be less than both of tensional intensity of the thread 3b and securing force of the needle body 3a to the thread 3b. The tensional intensity of the thread depends diameter and material of the thread, but under USPS, it is determined to be 960 gram-force for No. 3-0 thread, 1440 gram-force for No. 2-0 thread, 2160 gram-force for No. 1-0 thread, and 2720 gram-force for No. 1 thread as of the intensity when cut under a tensioned situation tying a knot (knot tying tension). The knot tying tension is less than simple tensional intensity. The securing force of the needle body 3a to the thread 3b is constituted of force given by caulking and frictional force between the thread 3b and the needle body 3a when the thread 3b is secured to the needle body 3a by caulking, and is constituted of adhesive intensity between the needle body 3a and the thread 3b when the thread 3b is fixed to the needle body 3a by the adhesive. Under USPS, the securing force of the needle body 3a to the thread 3b is determined to be depend on the thread diameter and the material of the thread, but under USPS, it is determined to be 680 gram-force for No. 3-0 thread, 1100 gram-force for No. 2-0 thread, 1500 gram-force for No. 1-0 thread, and 1800 gram-force for No. 1 thread. In consideration of the tensional intensity of the thread and the standard of the securing force, the holding force of the needle receiver 5 against the needle body 3a in this embodiment is set to be in a range between 250 and 500 gram-force.

The container 6 for containing the needle with thread 3 is formed at the parting face 2a of the second shaft 2. The container 6 contains the needle with thread 3 in cooperation of the both shafts 1, 2 when the shafts 1, 2 are closed and has a function for maintaining the holding situation while the shafts 1, 2 remain to be closed. The container 6 is constituted of a parting face 2a of the second shaft 2 and is formed, as originated from a position on the second shaft 2 opposed to the hole 1b formed on the first shaft 1, or namely as in continuation with the needle stand 5, in a groove shape having width substantially equal to or slightly less than the diameter of the needle body 3a of the needle with thread 3 and size sufficiently longer than the length of the needle body 3a.

When the shafts 1, 2 are made closed while the needle with thread 3 is contained in the container 6, the container 6 is covered by the parting face 1a of the first shaft 1, so that the container 6 prevents the needle with thread 3 from dropping out and surely contains the needle with thread 3. The container 6 does not have to be formed on the second shaft 2 and can be solely formed on the first shaft 1 if a groove is formed on the first shaft 1. In such a case, the second shaft 2 is formed with only the needle receiver 5 (see FIG. 8). The container 6 can be formed astride both shafts 1, 2 by forming grooves, each of which has the depth of subdivided container 6 in a depth direction, on the first and second shafts 1, 2 respectively (see FIG. 9). Whether the container 6 is formed solely on either the first shaft 1 or the second shaft 2 or whether container 6 is formed astride both shafts 1, 2 is an issue on the design and to be determined in accordance with size conditions of such as diameter of the needle body 3a of the needle with thread 3 and thickness of respective shafts 1, 2.

As shown in FIG. 1, a handle 7 is formed at the ends of the first and second shafts 1, 2 to allow a surgeon to manipulate to make the shafts pivotally move by inserting fingers of the surgeon into the handle 7. A guide 8 is formed for guiding the thread 3 along the first shaft 1; a holding member 9 for holding the thread 3 and a projection 10 for wounding the thread 3b are formed; a tension applying member 11 for applying tension to the thread 3b is formed at or in proximity of the handle 7.

The guide 8 has a function to let the thread 3b out smoothly without entangling the thread 3b with the first shaft 1 upon guidance of the thread 3b through the guide 8. The structure of the guide 8 is not limited as far as the guide 8 so functions. In this embodiment, the guide 8 is constituted of a hook-shaped member arranged with a certain interval on the first shaft 1.

The holding member 9 is for pushing, toward the first shaft 1, and holding the thread 3 guided along the first shaft 1 notwithstanding tension exerting to the thread 3b. The holding member 9 is therefore made of material having resilient nature capable of effectuating pushing force toward the first shaft 1. The holding member 9 is constituted to be capable of holding the thread 3b by the pushing force when the thread 3b is taken between the holding member 9 and the first shaft 1. The thread 3b is paid out along the first shaft 1 when the first and second shafts 1, 2 are separated while the needle with thread 5 is received by the needle receiver 5 after the blood vessels are ligated or incised areas are sutured. The holding force exerting to the thread 3b of the holding member 9 is therefore needed not to interfere with the paying out of the thread 3b and is adjustable by setting the pushing force of the holding member 9 toward the first shaft 1 in a proper range.

The projection 10 is in a tapered shape, whose neck to the first shaft 1 is made small, becoming larger in diameter thereof as going remote from the first shaft 1. The projection 10 provides tension to the thread 3b to maintain the stable securing condition of the needle with thread 3 when the needle body 3a is secured to the needle stand 4.

The tension applying member 11 has a function to make, when the jaws of the first and second shafts 1, 2 are made open while the needle with thread 3 is made to reach the affected area, the needle with thread 3 stand up at the needle stand 4 by pulling a prescribed length of the thread 3b in application of tension to the thread 3b. The structure of the tension applying member 11 is not limited as far as the tension applying member 11 functions so. In this embodiment, a pivotally movable lever is provided on and along the handle 7, and when the lever is moved pivotally in a direction of arrow a, the tension applying member holds the thread 3b and gives tension to the thread 3b, thereby permitting the thread 3b to travel in a direction of arrow b.

The tension applying member 11, in addition to make the needle with thread 3 contained in the container 6 stand up, is used for returning the needle with thread 3 which has been received by the needle receiver 5 after passing through or between the tissues to the needle stand 4 for passing through or between the tissues again. That is, for example, when the thread 3b is wrapped twice or more around the blood vessels at a time of ligation, the needle with thread 3 standing at the needle stand 4 is engaged with the needle receiver 5 upon closing movement of the first and second shafts 1, 2. The first and second shafts 1, 2 are then made open while the engagement between the needle with thread 3 and the needle receiver 5 is maintained, and the thread 3b is moved so as to be wrapped around the blood vessels. The first and second shafts 1, 2 are subsequently made close to let the needle body 3a of the needle with thread 3 contact with the needle stand 4, and upon tension's application to the thread 3b by controlling the tension applying member 11, the needle body 3a is made to be separated from the needle receiver 5 and to stand up at the needle stand 4. The needle with thread 3 is moved again, and the shafts 1, 2 are made close to engage the needle with thread 3 with the needle receiver 5. The shafts 1, 2 are then made open, and the needle with thread 3 is pulled out of the body of the patient while engaged with the needle receiver 5, thereby enabling the thread 3b to be wrapped twice around the blood vessels to perform ligations.

Referring now to FIGS. 1, 2, 5, 6, the open and close movement of the shafts 1, 2, positions and transfer movements of the needle with thread 3 are described below. It is to be noted that FIG. 5 (a) to (c) and FIG. 6 (a) to (c) indicate corresponding operations, respectively.

First, the handle 7 of the guide instrument A is manipulated to make the first and second shafts 1, 2 open, thereby opening the container 6 to contain the needle body 3a of the needle with thread 3. The needle body 3a is at that time contained so that the side of the proximal end surface 3a3 of the needle body 3a is placed to a side of the hole 1b formed on the shaft 1, and a part of the thread 3b remains out toward the tip of the second shaft 2. The handle 7 is controlled to make the shafts 1, 2 close, and the container 6 is covered by the first shaft 1. The closed position of the shafts 1, 2 are maintained by a stopper, and at the same time, the thread 3b is passed through the hole 1b by way of the slit 1c formed on the first shaft 1 and is wrapped around the projection 10. The thread 3b is also guided through the guide 8 along the first shaft 1, returning to the handle 7, engaging to the holding member 9 and then to the tension applying member 11 (see FIGS. 1, 2). Upon completion of those manipulations, the preparation of the guide instrument A for ligation and suture ends.

Under this situation, the shafts 1, 2 are already made closed, and the needle with thread 3 has been contained in the container 6 covered with the parting face 1a of the shaft 1 and has not been exposed to the outside of the instrument. Accordingly, even if the affected area is located at a deep or narrow area of the body, where the surgeon inserts the guide instrument A in the same sense to use regular forceps, the needle with thread 3 is never dropped off and can be reached to the affected area without damaging normal tissues by the needle body 3a.

Figure 6A:
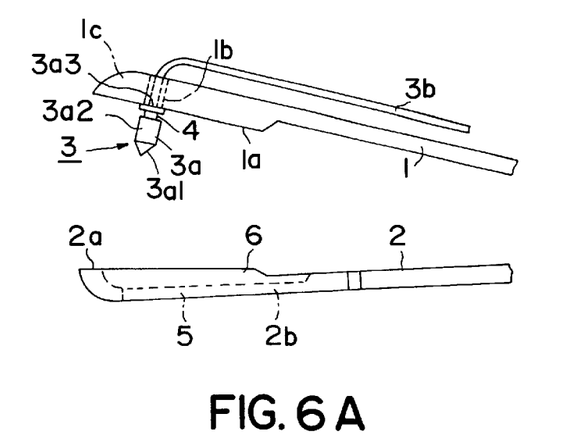
FIG. 6 shows illustrations for describing a transferring situation of the needle with thread upon open and close of the shafts at a time of ligation or suture.
Figure 6B:
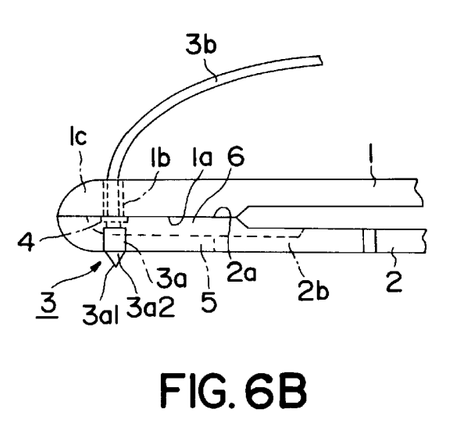
Figure 6C:
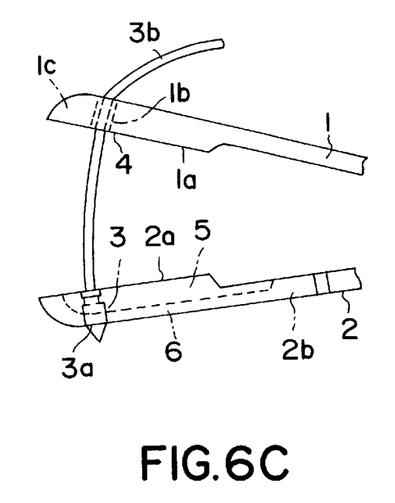
Figure 7A:
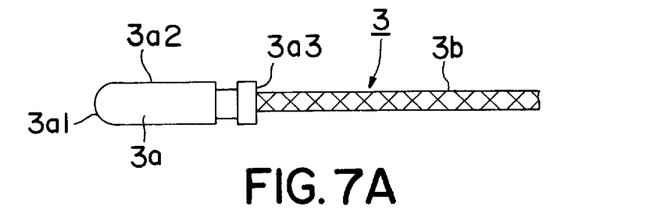
FIG. 7 shows illustration of other examples of the needle with thread.
Figure 7B:
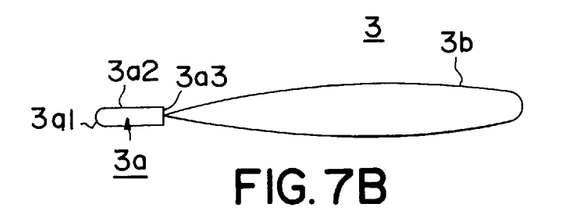
Figure 7C:
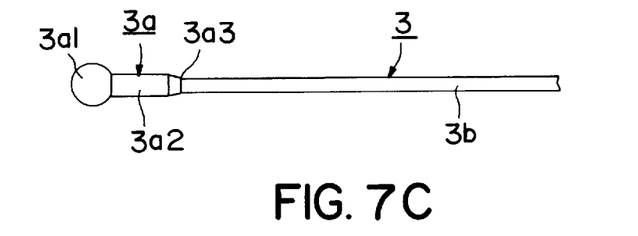
Figure 7D:
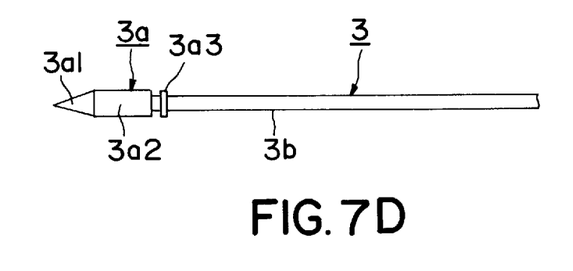

After the shafts 1, 2 are reached to the area of blood vessels E to be ligated, the stopper is released, and by manipulating the handle 7, the shafts 1, 2 are made open as shown in FIG. 5 (a). At the same time, tension is given to the thread 3b by manipulation of the tension applying member 11, and this power is transmitted to the needle body 3a through the thread 3d, thereby pulling the needle body 3a down to the hole 1b, thereby rotating the needle body 3a around the corner of the proximal end surface 3a3 in contact with the needle stand 4 formed inclusively with the hole 1b, and thereby rendering the needle body 3a stand up as shown in FIG. 6 (a).

The tip 3a1 of the needle body 3a, at that time, since moving through the slit 2b formed on the second shaft 2 and through space formed at the needle receiver 5 for receiving the needle body 3a, can keep sharpness of the tip 3a1 even though the tip 3a1 is made sharp pointed. The needle body 3a can keep standing upon holding the thread 3b at the holding member 9 while the needle body 3a is stood up at the needle stand 4.

Then, the shafts 1, 2 are made closed by manipulating the handle 7 under this situation, as shown in FIGS. 5 (b), 6 (b). During this closing process, the needle with thread 3 standing up at the needle stand 4 passes through or between the tissues surrounding the blood vessels E, and then, the tip 3a1 of the needle body 3a is inserted into the needle receiver 5. The barrel 3a2 is subsequently pushed into the needle receiver 5, and the needle receiver 5 holds the needle body 3a.

As shown in FIGS. 5 (c), 6 (c), where the shafts 1, 2 are subsequently made open by manipulation of the handle 7, the needle body 3a of the needle with thread 3 maintains to be held by the needle receiver 5, and the thread 3b is paid out through the hole 1b formed on the shaft 1 and through the guide 8, which are serving as a guide. The shafts 1, 2 are pulled out of the body as shown in FIG. 5 (d) while kept in this situation, thereby passing the thread 3b through or between tissues according to the movement of the needle body 3a, and thereby pulling the end of the thread 3b, which is attached to the needle body 3a, out of the body. The blood vessels E can be ligated by tying the pulled-out end and an end located on the side of the handle 7 of the thread 3b under this pulled situation.

Figure 8:
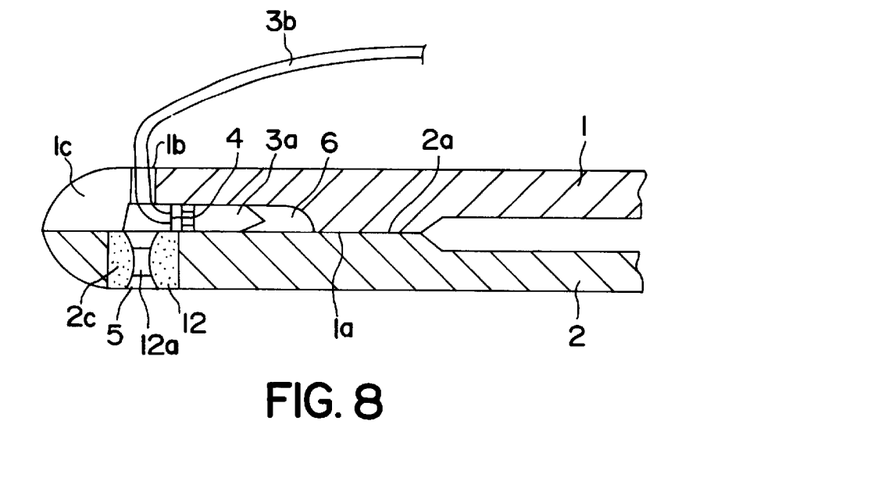
FIGS. 8, 9 are cross sections showing the respective essential portions of other embodiment of the guide instrument according to the invention.

FIG. 8 shows a modified example of the guide instrument in which the needle stand 4 and the container 6 are formed on the first shaft 1 and in which the needle receiver 5 is made of a resilient material. It is to be noted that in FIG. 8 the same portions and portions having the same functions as portions of the embodiment described above are assigned with the same numbers and those descriptions are omitted.

The hole 1b is formed on the first shaft 1 at a predetermined position. The slit 1c is formed between the hole 1b and the tip of the shaft 1. The needle stand 4 is formed on a surface in opposition to the shaft 2 inclusively in the vicinity of the hole 1b. The container 6 is formed of a groove, in continuation with the needle stand 4, having depth and width equal to or greater than the diameter of the needle body 3a of the needle with thread 3 and having length sufficiently longer than the length of the needle body 3a.

The needle receiver 5 is formed at a position on the second shaft 2 in opposition to the needle stand 4 formed on the first shaft 1. The needle receiver 5 is constituted to incorporated with a needle receiving member 12 having a prescribed shape provided in a hole 2c bored through the second shaft 2 in the thickness direction of the shaft 2. The needle receiving member 12 is made of a resilient body such as synthetic rubber, for example, urethane rubber or the like, and natural rubber, or a magnetic body, has length substantially equal to the thickness of the second shaft 2 and outer diameter substantially equal to or a little greater than the diameter of the hole 2c formed in the second shaft 2, and is formed with a holding hole 12a inside thereof. The holding hole 12a has diameter a little smaller than the diameter of the needle body 3a of the needle with thread 3 when the needle receiving member 12 is made of the resilient body and has diameter equal to the diameter of the needle body 3a when the needle receiving member 12 is made of the magnetic body. The needle receiver 5 is structured by fitting the needle receiving member 12 into the hole 2c of the second shaft 2 to make the member 12 adhere or by pushing the member 12 into the hole 2c.

Even if the needle receiver 5 and the container 6 are thus formed, the needle with thread 3 can be stood up at the needle stand 4 by a manipulation in the same fashion as described above, and ligations and sutures are performed by passing the thread 3b through or between the tissues.

FIG. 9 shows another modified embodiment of the guide instrument in which the needle stand 4 with a stepwise stage capable of containing the needle body 3a of the needle with thread 3 is formed on the first shaft 1 and in which the container 6 is formed astride the first and second shafts 1, 2. It is to be noted that in FIG. 9 the same portions and portions having the same functions as portions of the embodiment described above are assigned with the same numbers and those descriptions are omitted.

In FIG. 9, a stepwise stage 4a extending annularly is formed around the hole 1b formed in the shaft 1; the needle stand 4 is constituted of the stepwise stage 4a. A relationship between the diameter of the stepwise stage 4a and diameter of the needle body 3a of the needle with thread 3 is not specifically limited; when the diameter of the stepwise stage 4a is greater than the diameter of the needle body 3a, the needle body 3a engages the stepwise stage 4a at the proximal end surface 3a3 and stands up; when the diameter of the stepwise stage 4a is substantially equal to the diameter of the needle body 3a, the needle body 3a engages the stepwise stage 4a with the proximal end surface 3a3 as well as the stepwise stage 4a contacts the outer circumferential surface of the needle body 3a, so that the needle body 3a is stood up; when the diameter of the stepwise stage 4a is smaller than the diameter of the needle body 3a, the needle body 3a engages the edge of the stepwise stage 4a with a part of the barrel 3a2 on the side of the proximal end surface 3a3 and stands up.

Figure 9A:
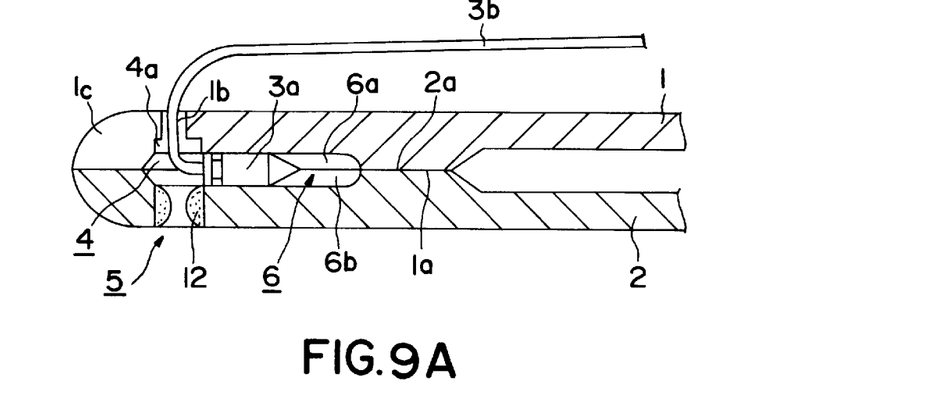
Figure 9B:
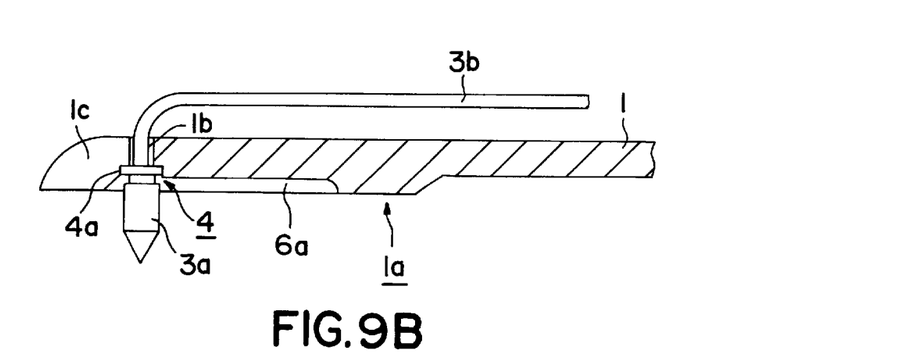

On the parting faces 1a, 2a on the first and second shafts 1, 2, formed are grooves 6a, 6b having width and depth sharing size equal to or larger than the diameter of the needle body 3a and having length longer than the length of the needle body 3a, and these grooves 6a, 6b constitute the container 6. The needle receiver 5 is formed at a position on the second shaft 2 in opposition to the hole 1b and the stepwise stage 4a formed in the first shaft 1. The needle receiving member 12 made of a resilient body or magnetic body is disposed at the needle receiver 5.

Where the container 6 is formed astride the first and second shafts 1, 2 as described above, equalizing the thickness corresponding to the grooves 6a, 6b of the shafts 1, 2 as shown in FIG. 9 (a) makes structural intensity improve and allows the needle with thread 3 to be contained stably. Where the needle stand 4 is formed by the stepwise stage 4a formed around the hole 1b formed in the first shaft 1, the proximal end of the needle body 3a can be fitted into the stepwise stage 4a by separating the shafts 1, 2 and by applying tension to the thread 3b of the needle with thread 3 contained in the container 6, as shown in FIG. 9 (b), thereby enabling the needle body 3a to stand up while the bottom surface of the stepwise stage 4a is in contact with the proximal end surface 3a3 or while the outer periphery of the proximal end of the barrel 3a2 engages the edge of the stepwise stage 4a. As described above, where the needle stand 4 is formed by the stepwise stage 4a formed around the hole 1b, the needle with thread 3 can stand up at the fixed position, thereby rendering stable the transfer of the needle with thread from the needle stand 4 to the needle receiver 5 at a time of ligation or suture.

Figure 10A:
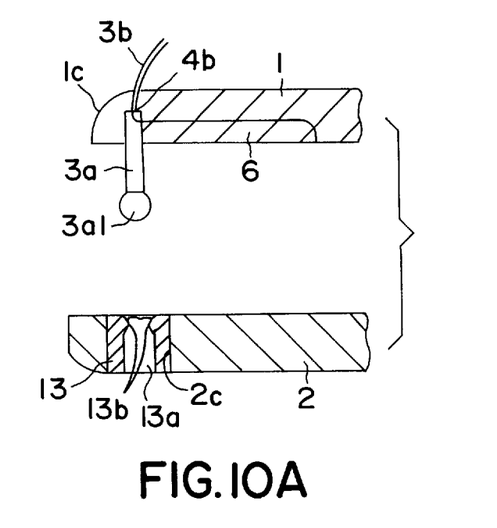
FIG. 10 shows illustrations of another needle receiver of the guide instrument according to the invention.

FIG. 10 shows a modification of the guide instrument A using the needle with thread 3 shown in FIG. 7 (c) and a needle receiver 5 receivable of the spherical body formed at the needle body 3a of the needle with thread 3. The needle receiver 5 is constituted of a needle receiving member 13, made of a resilient body, pushed into or adhering to the hole 2c formed in the second shaft 2. The needle receiving member 13 is formed with a hole 13a for receiving the spherical tip 3a1 formed at the needle body 3a of the needle with thread 3 and formed with a projection 13b to prevent the tip 3a1 engaged in the hole 13a from disengaging from the hole 13a.

Figure 10B:
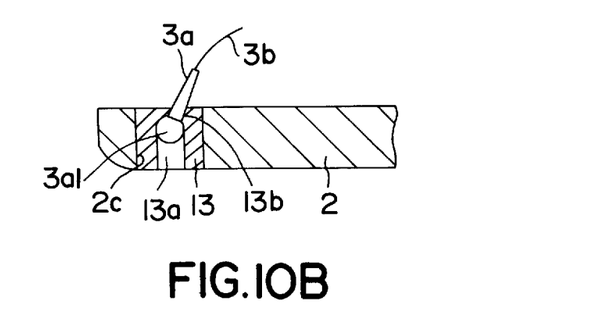

With the guide instrument A thus constituted, when the tip 3a1 of the needle body 3a of the needle with thread 3 engages the hole 13a of the needle receiving member 13, the engagement between the needle body 3a and the needle receiver 5 is maintained even if the first and second shafts 1, 2 are made open. After the guide instrument A is pulled out of the body, if the surgeon as shown in FIG. 10 (b) pulls the thread 3b so that the thread 3b comes in parallel to the second shaft 2, the proximal end of the tip 3a1 engages the projection 13b, and the needle body 3a is pivotally moved around the engaged point, thereby enabling the needle body 3a to separate from the needle receiving member 13.

Figure 11:
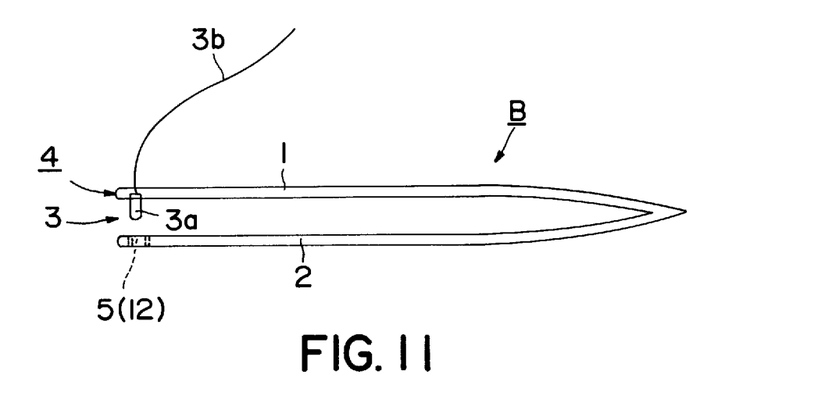
FIGS. 11, 12 are illustrations showing, respectively, other modifications of the guide instrument.

FIG. 11 shows a guide instrument B in which the first and second shafts 1, 2 are connected at their ends and pivotally move against each other in providing resilient nature to the shafts. The guide instrument B can be controlled by a surgeon in the same sense of the use of forceps. The guide instrument B is formed so that jaws (on the left side in FIG. 11) of the first and second shafts 1, 2 have proper rigidity and that on the proximal side (on the right side in FIG. 11) the shafts 1, 2 are connected with resiliency. The guide instrument B, even though constituted thus, can receive, by the needle receiver 5 (or the needle receiving member 12) formed on the jaw of the second shaft 2, the needle with thread 3 stood up at the needle stand 4 formed at the jaw of the first shaft 1.

Figure 12:
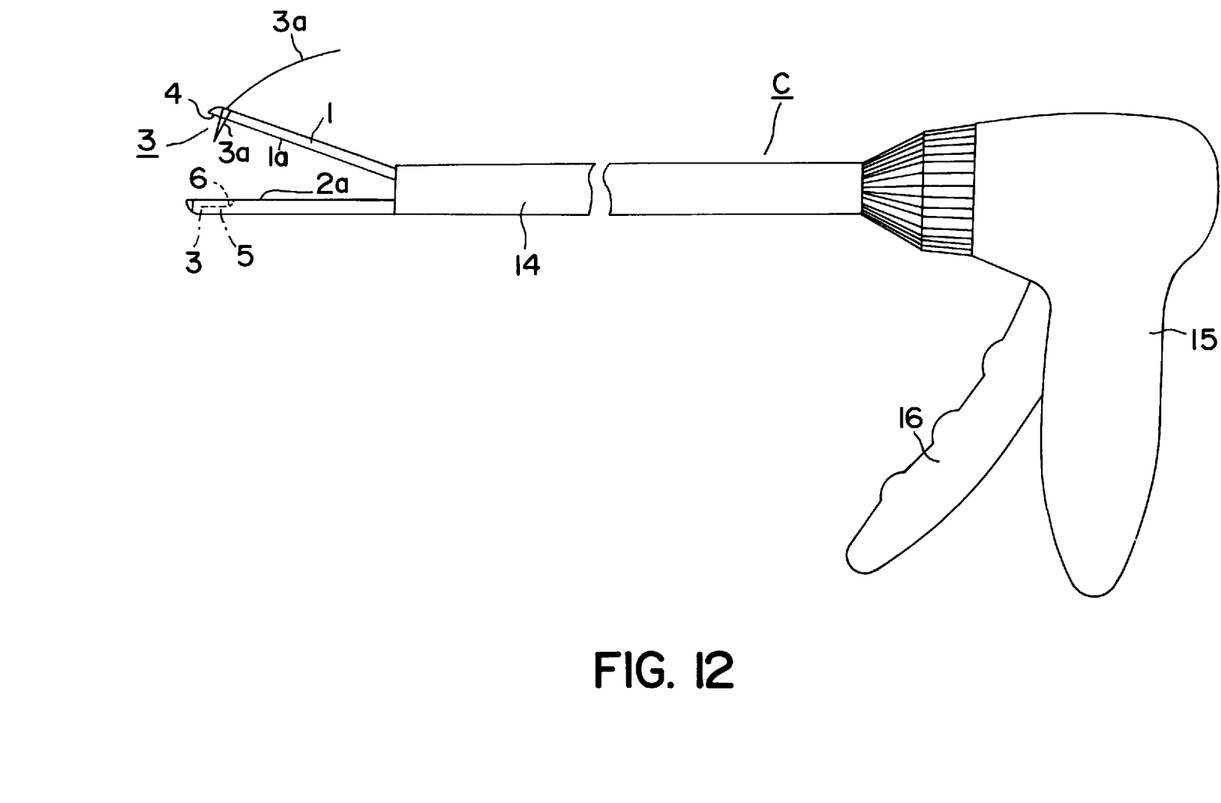

The first and second shafts 1, 2 do not have to be formed unitedly with the handle 7 as of the guide instrument A and can be formed in a manner of a guide instrument C shown in FIG. 12. In FIG. 12, the shafts 1, 2 are disposed on a tip of a casing 14 having a prescribed length (in accordance with depth of the affected area, for example, of 300 to 400 millimeters); one shaft, for example, the second shaft 2 formed with the needle receiver 5 and the container 6, is fixedly connected to the casing 14; the other shaft, for example, the first shaft 1 formed with the needle stand 4, is pivotally mounted to the casing 14. The rear end of the casing 14 is secured to a handle grip 15 to which a trigger 16 is arranged. The first shaft 1 is connected to the trigger 16 through a transmission member such as a wire or rod provided within the casing 14; the first shaft 1 can be moved pivotally according to manipulation of the trigger 16 and approach the second shaft 2.

With the guide instrument thus constituted, the affected area located in a deep position of the body can be ligated or sutured. In particular, forming the casing 14 in use of a flexible material allows the guide instrument to widely applied, for example, for laparoscopy or the like.

The foregoing description of a preferred embodiment of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not to be limited by the specification, but be defined by the claims set forth below.

What is claimed is:

1. A guide instrument for a medical needle with thread in which the medical needle with thread, which includes a needle body and a thread secured to a proximal end of the needle body extending in an elongated direction of the needle body is made to pass through or between body tissues and in which the medical needle that has passed therethrough is received, the guide instrument comprising:

a pair of shafts pivotally mounted to each other having a handle on the shafts for manipulation;

a needle stand formed on a distal end of one of the shafts for rendering the needle body stand up by contacting, the needle stand is constituted of a recess in contact with either both of the surfaces of the proximal end of the needle body and a part of the outer circumferential surface located on the proximal side of the needle body or the surface of the proximal end of the needle body, the needle stand having a flat surface to be in contact with the surface of the proximal end of the needle body;

a thread guide formed on the distal end of one of the shafts for guiding the thread in communication with the needle stand; and a needle receiver formed on a distal end of the other of the shafts for receiving the needle body that stands, the needle receiver constituted of a long hole or slit having width substantially equal to or slightly less than the diameter of the needle body and extending toward a distal end and/or a proximal end of the shaft from a position on the other shaft corresponding to the needle stand formed on the one shaft, whereby while the distal ends of shafts are made close, the needle body standing upon one of the shafts is rushed to pass through or between body tissues and to be engaged with the needle receiver formed at the other of the shafts, and while the distal ends of the shafts are made open, the needle body maintains the engagement with the needle receiver to be separated from the needle stand;

wherein the needle receiver formed on the distal end of the other shaft is constituted of a long hole having width substantially equal to or slightly less than the diameter of the needle body and extending toward a distal end and/or a proximal end of the shaft from a position on the other shaft corresponding to the needle stand formed on the one shaft;

wherein the needle receiver constituted of the long hole has holding force of the needle body less than tensional intensity of the thread secured to the needle body or securing force of the needle body to the thread.

2. A guide instrument for a medical needle with thread in which the medical needle with thread, which includes a needle body and a thread secured to a proximal end of the needle body extending in an elongated direction of the needle body, is made to pass through or between body tissues, and in which the medical needle that has passed therethrough is received, the guide instrument comprising:

a pair of shafts pivotally mounted to each other having a handle on the shafts for manipulation;

a needle stand formed on a distal end of one of the shafts for rendering the needle body stand up by contacting, the needle stand is constituted of a recess in contact with either both of the surfaces of the proximal end of the needle body and a part of the outer circumferential surface located on the proximal side of the needle body or the surface of the proximal end of the needle body, the needle stand having a flat surface to be in contact with the surface of the proximal end of the needle body;

a thread guide formed on the distal end of one of the shafts for guiding the thread in communication with the needle stand; and a needle receiver formed on a distal end of the other of the shafts for receiving the needle body that stands the needle receiver constituted of a lone hole or slit having width substantially equal to or slightly less than the diameter of the needle body and extending toward a distal end and/or a proximal end of the shaft from a position on the other shaft corresponding to the needle stand formed on the one shaft, whereby while the distal ends of shafts are made close, the needle body standing up on one of the shafts is pushed to pass through or between body tissues and to be engaged with the needle receiver formed at the other of the shafts, and while the distal ends of the shafts are made open, the needle body maintains the engagement with the needle receiver to be separated from the needle stand:

wherein the one shaft is formed with a tension applying member for applying tension to the thread guided along the one shaft.

3. A guide instrument for a medical needle with thread in which the medical needle with thread, which includes a needle body and a thread secured to a proximal end of the needle body extending in an elongated direction of the needle body, is made to pass through or between body tissues and in which the medical needle that has passed therethrough is received, the guide instrument comprising:

a pair of shafts pivotally mounted to each other having a handle on proximal ends of the shafts for manipulation;

a needle stand formed on a distal end of one of the shafts for rendering the needle body stand up by contacting either or both of a proximal end of the needle body and a part of the circumferential surface located on a proximal side of the needle body;

a thread guide formed on the distal end of one of the shafts for guiding the thread in communication with the needle stand;

a needle receiver formed on a distal end of the other of the shafts for receiving the needle body that stands;

a horizontal needle container lying in the same plane as the pair of shafts for holding the needle body lying down formed continuously to either or both of the needle stand or the needle receiver, whereby while the distal ends of shafts are made open or after distal ends of shafts are made open, the needle body lying down on the needle container is made stand up, and while the distal ends of shafts are made close, the needle body standing up on one of the shaft is pushed to pass through or between body tissues and to be engaged with the needle receiver formed at the other of the shafts, and while the distal ends of the shafts are made open, they are separated from the needle stand.

4. The guide instrument according to claim 3, wherein the needle stand formed on the distal end of the one shaft is constituted of a flat surface to be in contact with the surface of the proximal end of the needle body.

5. The guide instrument according to claim 3, wherein the thread guided formed on the distal end of the one shaft is constituted so that a corner of the thread guide located at a passage of the thread does not damage the thread.

6. The guide instrument according to claim 3, wherein the needle stand formed on the distal end of the one shaft is constituted of a recess in contact with either or both of the surface of the proximal end of the needle body and a part of the outer circumferential surface located on the proximal side of the needle body.

7. The guide instrument according to claim 3, wherein the needle receiver formed on the distal end of the other shaft is constituted of a long hole having width substantially equal to or slightly less than the diameter of the needle body and extending toward a distal end and/or a proximal end of the shaft from a position on the other shaft corresponding to the needle stand formed on the one shaft.

8. The guide instrument according to claim 7, wherein the needle receiver constituted of the long hole formed on the other shaft is formed with a slit extending toward the distal end and/or the proximal end of the shaft from a long hole.

9. The guide instrument according to claim 7, wherein the needle receiver constituted of the long hole has holding force of the needle body less than tensional intensity of the thread secured to the needle body or securing force of the needle body to the thread.

10. The guide instrument according to claim 3, wherein the one shaft is formed with a guide for guiding along the one shaft the thread secured to the needle body.

11. The guide instrument according to claim 3, wherein the one shaft is formed with a holding member for holding the thread guided along the one shaft and secured to the needle body.

12. The guide instrument according to claim 3, wherein the one shaft is formed with a tension applying member for applying tension to the thread guided along the one shaft.

13. The guide instrument according to claim 3, wherein the one shaft is formed with a projection for wrapping the thread guided along the one shaft.

14. The guide instrument according to claim 3, wherein the needle body of the medical needle with thread is a straight needle having length equal to or greater than 3 millimeters and less than 15 millimeters.

15. The guide instrument according to claim 3, wherein the needle body of the medical needle with thread has diameter twice or more of the diameter of the thread.

* * * * *